(12) United States Patent
Kennedy

(10) Patent No.: US 8,962,027 B2
(45) Date of Patent: Feb. 24, 2015

(54) MATERIALS COMPRISING WATER-SOLUBLE POLYMER PARTICLES AND METHODS OF MAKING AND USING THEM

(75) Inventor: T. Scott Kennedy, East Boothbay, ME (US)

(73) Assignee: Rynel Inc., Wiscasset, ME (US)

( * ) Notice: Subject to any disclaimer, the term of this patent is extended or adjusted under 35 U.S.C. 154(b) by 1239 days.

(21) Appl. No.: 12/665,178

(22) PCT Filed: Jun. 19, 2008

(86) PCT No.: PCT/US2008/067528
§ 371 (c)(1),
(2), (4) Date: Mar. 9, 2011

(87) PCT Pub. No.: WO2008/157711
PCT Pub. Date: Dec. 24, 2008

(65) Prior Publication Data
US 2011/0171282 A1 Jul. 14, 2011

Related U.S. Application Data

(60) Provisional application No. 60/944,860, filed on Jun. 19, 2007.

(51) Int. Cl.
| | |
|---|---|
| *A61K 9/14* | (2006.01) |
| *A61K 9/70* | (2006.01) |
| *C08F 2/18* | (2006.01) |
| *A61K 31/74* | (2006.01) |
| *C08G 18/10* | (2006.01) |

(Continued)

(52) U.S. Cl.
CPC . *C08F 2/18* (2013.01); *A61K 31/74* (2013.01);
*C08G 18/10* (2013.01); *C08G 18/14* (2013.01);
*C08J 9/0061* (2013.01); *C08G 2101/00*
(2013.01); *C08J 2375/04* (2013.01); *C08J 2471/00* (2013.01)
USPC .......................................... 424/489; 424/443

(58) Field of Classification Search
None
See application file for complete search history.

(56) References Cited

U.S. PATENT DOCUMENTS

| | | | |
|---|---|---|---|
| 2,381,621 | A | 8/1945 | Schmelkes et al. |
| 2,804,425 | A | 8/1957 | Smith et al. |

(Continued)

FOREIGN PATENT DOCUMENTS

| | | | |
|---|---|---|---|
| CA | 486203 | A | 9/1952 |
| CA | 503389 | A | 6/1954 |

(Continued)

OTHER PUBLICATIONS

International Search Report for PCT/US2008/067528 dated Dec. 17, 2008.

(Continued)

*Primary Examiner* — Nissa Westerberg
(74) *Attorney, Agent, or Firm* — Dana M. Gordon; Foley Hoag LLP

(57) ABSTRACT

One aspect of the invention relates to new materials for storing, protecting, selectively releasing, and applying active ingredients (e.g. pharmaceuticals and other chemicals). In certain embodiments, the invention provides materials impregnated with water-soluble polymer particles which contain active ingredients which may be selectively released and dispensed in response to contact with water or another liquid.

14 Claims, 1 Drawing Sheet

(51) Int. Cl.
*C08G 18/08* (2006.01)
*C08J 9/00* (2006.01)
*C08G 101/00* (2006.01)

(56) References Cited

U.S. PATENT DOCUMENTS

| | | |
|---|---|---|
| 3,194,773 A | 7/1965 | Hostettler |
| 3,238,273 A | 3/1966 | Hampson et al. |
| 3,336,242 A | 8/1967 | Hampson et al. |
| 3,380,967 A | 4/1968 | Lowe et al. |
| 3,457,203 A | 7/1969 | Cohen et al. |
| 3,461,086 A | 8/1969 | Mogford et al. |
| 3,546,145 A | 12/1970 | Granger et al. |
| 3,817,702 A | 6/1974 | Paulus et al. |
| 3,910,230 A | 10/1975 | Mercer |
| 3,966,902 A | 6/1976 | Chromecek |
| 3,987,793 A | 10/1976 | Milnamow |
| 4,246,668 A | 1/1981 | Spillmann et al. |
| 4,549,011 A | 10/1985 | Herzberg et al. |
| 4,585,652 A | 4/1986 | Miller et al. |
| 4,597,960 A * | 7/1986 | Cohen ............... 424/435 |
| 4,664,662 A * | 5/1987 | Webster ............. 602/47 |
| 4,828,542 A | 5/1989 | Hermann |
| 4,997,425 A * | 3/1991 | Shioya et al. ......... 604/304 |
| 5,098,621 A | 3/1992 | Hermann |
| 5,607,474 A * | 3/1997 | Athanasiou et al. ....... 623/23.71 |
| 5,977,014 A * | 11/1999 | Plischke et al. ............. 502/401 |
| 6,221,399 B1 * | 4/2001 | Rolfes et al. ............... 424/489 |
| 2002/0022884 A1 * | 2/2002 | Mansmann ............ 623/14.12 |
| 2004/0109992 A1 | 6/2004 | Gribble et al. |
| 2005/0003178 A1 | 1/2005 | Detert et al. |
| 2009/0264845 A1 * | 10/2009 | Himori et al. ............... 604/367 |

FOREIGN PATENT DOCUMENTS

| | | | |
|---|---|---|---|
| CA | 547091 A | | 10/1957 |
| CA | 588169 A | | 12/1959 |
| CA | 823628 A | | 9/1969 |
| CA | 839229 A | | 4/1970 |
| CA | 1049407 A1 | | 2/1979 |
| CA | 2381621 A1 | | 2/2001 |
| GB | 1429711 A | * | 11/1978 |
| GB | 2007096 A | | 5/1979 |
| WO | WO 2006011625 A1 | * | 2/2006 |

OTHER PUBLICATIONS

Written Opinion for PCT/US2008/067528 dated Dec. 17, 2008.
Extended European Search Report for EP 08771497.8 dated Dec. 6, 2010.

* cited by examiner

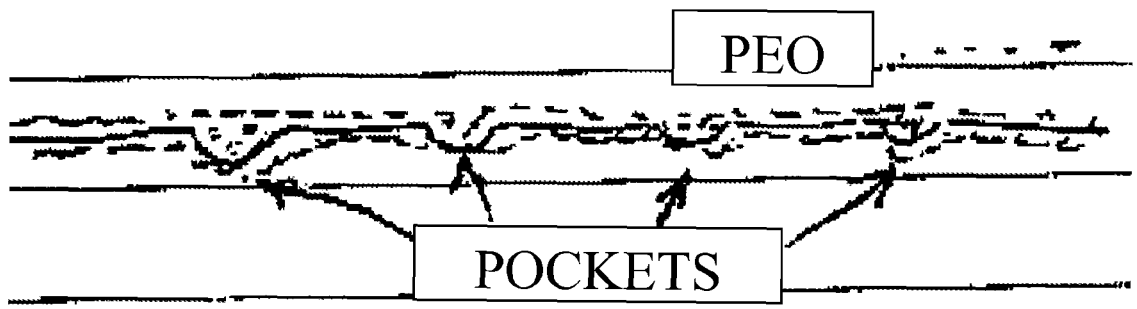

US 8,962,027 B2

MATERIALS COMPRISING WATER-SOLUBLE POLYMER PARTICLES AND METHODS OF MAKING AND USING THEM

RELATED APPLICATIONS

This application is the U.S. National Stage of International Patent Application No. PCT/US2008/067528, filed Jun. 19, 2008, which claims the benefit of priority to U.S. Provisional Patent Application Ser. No. 60/944,860, filed Jun. 19, 2007; both of which are hereby incorporated by reference in their entireties.

BACKGROUND

When drugs are systemically administered to treat wounds (including cuts, abrasions, incisions, ulcers and infected wounds or burns), a large portion of the drugs is either degraded or adsorbed by non-target tissues and only a small portion of the initial dose reaches the target site. The efficiency of systemic dosing is further decreased in the trauma patient (as in accidents, earthquakes, fires and wars) who often suffer a decreased vascular flow and thus have reduced drug circulation. Furthermore, the trauma patient often fails to provide information regarding sensitivity to drugs, or fails to take drugs orally. Topical drug administration, in theory, would provide immediate, direct, and sustained effects at the target site, and reduce side-effects and degradation of drugs encountered in systemic dosing. Topical application also permits rapid removal and replacement of drugs when adverse effects are noticed. When cleansing is not readily available, topical application is more effective in destroying microbial spores because a higher concentration of drugs can be applied. Thus, treatment of wounds or burns will benefit from an improvement of topical administration, whether used alone or in conjunction with systemic dosing.

Currently, antibiotics, e.g. fusidic acid, chlorohexidine, Neomycin, Polymyxin and Bacitracin are topically applied in gel, cream or ointment forms (occasionally in aerosol and powder). Because a high concentration of the drugs are in direct contact with the target tissue, some of the drugs cause allergic reaction by contact with the target tissue, some of drugs cause allergic dermatitis, particularly in patients with stasis ulcers or eczema, or exhibit toxicity.

The absorption of drugs on carriers is known in the art. For example, Canadian Patent No. 486,203 to Johnson & Johnson taught the use of gauze, as a carrier, Canadian Patent No. 503,389 to Casumano taught the use of gauze pads, as a carrier, and Canadian Patent No. 823,628 to Wyant used paper toweling as a carrier.

Canadian Patent No. 547,091 to Lerner used materials, e.g. aluminum foil, regenerated cellulose sheets or impervious, grease-proof glassine paper, which have non-capillary faces as carriers.

Canadian Patent No. 588,169 to Chicopee used non-woven fabrics, optionally bonded with internally-plasticized polyvinyl acetates.

Canadian Patent No. 839,229 to Astra used sheets of water-soluble, film-forming compounds.

Canadian Patent No. 1,049,407 to Pharmacia used water-insoluble, hydrophilic macromolecular materials.

U.S. Pat. No. 2,381,621 patented Aug. 7, 1945 by Wallace & Tiernan Products, Inc. taught a therapeutic article including a base material comprising a thin, pliable, hydrophilic, non-porous but water-penetrable material in film form and a plurality of water-soluble medicinal substances distributed by being absorbed but not ionically bound to the base material.

U.S. Pat. No. 2,804,425 patented Aug. 27, 1957 by American Cyanamid Company taught a sterile, anhydrous, storage-stable chlortetracycline-containing wound packing comprising a lintless, heavy-metal-free gauze impregnated with, but not ionically-bonded to, chlortetracycline.

U.S. Pat. No. 3,817,702 patented Jun. 18, 1974 by Bayer Aktiengessellschaft taught an antimicrobial textile material comprising a textile material containing reactive hydrogen sites, e.g. cotton treated with a reagent to introduce anion-active sites, which was then chemically reacted with a biocide to form a salt of the biocide with the textile material. The textile material thus became anion-active, and was finished by treatment with a cation-active microbiocide the ionic bond being so strong as to provide a lastingly, partially anion-active textile material.

U.S. Pat. No. 3,987,793 patented Oct. 26, 1976 by Ethicon Inc. provided a surgical suture which was coated with a ionically-bonded, block elastomeric copolymer so that it was receptive to treatment with antimicrobial compounds the bonding between the copolymer and the antimicrobial compound being so strong as to produce a substance having long-lasting antimicrobial properties.

U.S. Pat. No. 4,549,011 patented Oct. 22, 1985 by Orgenics Ltd. provided a sheet of cellulose or plastic material which was activated with a compound which can covalently bind a liquid thereto, and then a ligand is then coated on the sheet. The ligand is one having an affinity for a substance to be separated from a mixture of substances.

U.S. Pat. No. 4,585,652 patented Apr. 29, 1986 by Regents of the University of Minnesota provided a controlled drug release system comprising a polymer which, in its ionic state, was loaded with bioactive counterions. When the polymer was neutralized the counterions were released into the surrounding medium. The patentee used an electrode comprising a polymer which changed its ionic state for loading and for discharging purposes. This was an unnecessarily complicated system and did not have practicability for general use.

U.K. Patent Application GB 2007096 A published 16th of May, 1979 provided an indicator to show when an antimicrobial composition, which was impregnated in, but not ionically bonded to, a cloth was no longer present in the cloth. The antimicrobial composition was ionically-bonded to a dye, so that when the antimicrobial composition was exhausted from the cloth, the dye also was exhausted, and so no color remained.

To provide a controlled release of drugs, a U.S. Army medical team had developed microcapsules (diameters of <10μ) containing ampicillin for topical application to wound sites. However, these delivery systems (gel, cream, ointment, powder and microcapsule) suffer a practical problem: their even application or removal to and from the target site requires gentle manipulation and is too time-consuming for treatment of a large number of trauma patients in emergency cases.

To overcome this problem, gauze dressings impregnated with a suspension of antibiotics (e.g., fusidic acid and Neomycin) in appropriate media (e.g., petroleum jelly and lanolin) had also been developed. However, such delivery system did not control the release of drugs and thus did not solve the allergy or toxicity problems. Furthermore, the dressings impregnated with gel or liquid did not adsorb the exudate, and may not have provided sufficient breathability which would be desired for the treatment.

Enzymes, e.g. fibrinolytic proteases and deoxyribonucleases, have occasionally been used to dissolve fibrous or purulent accumulations in infected wounds or burns. These enzymes are currently applied in the form of gels (e.g., carboxymethyl cellulose gel) or ointments. Such systems would suffer the same problems of allergy and time-consuming application described above. Furthermore, they did not provide mechanisms for removal of enzymic hydrolysates which are potential irritants.

Apparatus for the treatment of textiles with aqueous solutions of treating agents are also known in the art. For example, U.S. Pat. No. 3,910,230, patented Oct. 7, 1975, by H. L. Mercer, provided an apparatus for applying a desired percentage by weight of liquid to a running textile fabric.

U.S. Pat. No. 2,426,668, patented Jan. 27, 1981, by W. Spillmann et al, provided apparatus and methods for the treatment of a web or a number of webs of material guided side by side in the nip between treatment rollers, the web or webs of material being impregnated with or containing treating agents.

U.S. Pat. No. 3,817,702, patented Jun. 18, 1974, by Bayer Aktiengesellschaft provide a laboratory-scale procedure for preparing textile materials lastingly protected from staining by damp and mildew and from rotting by a cation-active microbial. The process taught involved impregnated the fabric, squeezing off the excess, and then drying the fabric. The cation-active microbial was then absorbed by the fabric from an aqueous solution. The excess was squeezed off and unfixed portions of the active compound was washed away.

However, even given the materials discussed above, there is still a need for novel materials which control the release of drugs and/or address the allergy or toxicity related-problems.

SUMMARY

One aspect of the invention relates to new materials for storing, protecting, selectively releasing, and applying active ingredients (e.g. pharmaceuticals and other chemicals). In certain embodiments, the invention provides foam coated substrates comprising active-ingredient containing water-soluble polymer particles; such materials may be used for selectively releasing and dispensing active ingredients in response to contact with water or another liquid. In certain embodiments, the foam is a hydrophilic foam, a hydrophobic foam, or a hydrogel. In certain embodiments, the foam is a hydrophobic polyurethane foam. In certain embodiments, the water-soluble polymer particles are ethylene oxide particles. In certain embodiments, the impregnated foam is a polyurethane foam impregnated with polyethylene oxide particles.

One aspect of the invention relates to a material comprising a substrate, a foam, and a plurality of water-soluble polymer particles; wherein each of the plurality of water-soluble polymer particles comprise an active ingredient, the foam permeates the substrate, and the water-soluble polymer particles are trapped within the substrate by the foam.

Another aspect of the invention relates to a material comprising a substrate, two layers of foam, and a plurality of water-soluble polymer particles; wherein each of the plurality of water-soluble polymer particles comprise an active ingredient, the substrate is sandwiched between the two layers of foam, and the water-soluble polymer particles are trapped within the substrate by the two layers of foam.

In certain embodiments, the present invention relates to the any of the aforementioned materials, wherein the substrate is a non-woven material. In certain embodiments, the present invention relates to the any of the aforementioned materials, wherein the substrate is an aperture non-woven material. In certain embodiments, the present invention relates to the any of the aforementioned materials, wherein the substrate is a non-woven material comprising a mesh surface. In certain embodiments, the present invention relates to the any of the aforementioned materials, wherein the substrate is a non-woven fabric or a non-woven cloth.

In certain embodiments, the present invention relates to the any of the aforementioned materials, wherein the foam is a polyurethane foam prepared from water, a surfactant, and a prepolymer mixture.

In certain embodiments, the present invention relates to the any of the aforementioned materials, wherein the surfactant is selected from the group consisting silcone-based surfactants, polysiloxane-polyoxyalkylene block copolymers, cyanoalkylpolysiloxanes, alkylpolysiloxanes, polydimethylsiloxane, polyoxyalkylene-modified dimethylpolysiloxanes, salts of fatty acids, salts of sulfuric acid esters, salts of phosphoric acid esters and sulfonates, TRITON™ (e.g., ocetylphenol ethoxylate) materials, TERGITOL™ (e.g., nonylphenol ethoxylate) materials, EMEREST® (glycerol esters with stearic, oleic, and isostearic fatty acids) materials, EMULGADE® (cetearyl alcohol and/or stearate-containing emulsifier) materials, Cocamide monoethanolamine (MEA), PLURONIC® (polyoxyethylene-polyoxypropylene-polyoxyethylene polymer) materials, BRIJ® 72 (polyoxyethylene (2) stearyl ether) and sodium alpha olefin sulfonate. In certain embodiments, the present invention relates to the any of the aforementioned materials, wherein the surfactant is polyoxyalkylene-modified dimethylpolysiloxanes.

In certain embodiments, the present invention relates to the any of the aforementioned materials, wherein the prepolymer mixture selected from the group consisting of branched alkyl-isocyanate-capped poly(ether), unbranched alkyl-isocyanate-capped poly(ether), branched aromatic-isocyanate-capped poly(ether), unbranched aromatic-isocyanate-capped poly(ether), branched alkyl-isocyanate-capped poly(ether)-poly(ester) copolymer, unbranched alkyl-isocyanate-capped poly(ether)-poly(ester) copolymer, branched aromatic-isocyanate-capped poly(ether)-poly(ester) copolymer, and unbranched aromatic-isocyante-capped poly(ether)-poly(ester) copolymer. In certain embodiments, the present invention relates to the any of the aforementioned materials, wherein the prepolymer mixture is toluene diisocyanate terminated or capped polyethylene glycol with less than 6% available unreacted NCO groups and with an isocyanate functionality less than 2.

In certain embodiments, the present invention relates to the any of the aforementioned materials, wherein the water-soluble polymer particles are prepared from one or more monomers selected from the group consisting of styrene, vinyl acetate, ethylene, ethylene oxide, acrylonitrile, acrylic acid, acrylamide, maleic anhydride, monovinyl silicon compounds, ethyl vinyl ether, chlorostyrene vinyl pyridine, vinylidene chloride, butyl vinyl ether, methyl methacrylate and 2-ethylhexyl acrylate In certain embodiments, the present invention relates to the any of the aforementioned materials, wherein the water-soluble polymer particles are polyethylene oxide polymer particles or polyethylene glycol polymer particles.

In certain embodiments, the present invention relates to the any of the aforementioned materials, wherein the active ingredient is selected from the group consisting of silver salts, silver nitrate, silver sulfate, nafcillin, nystatin, undecylenic acid, salicylic acid, salicylsulfonic acid, nicotinic acid, adenosine diphosphate, chlorhexidine, bacitracin, chlortetracycline, gentamycin, kanamycin, neomycin B, polymyxin B, streptomycin, tetracycline, amphotericin B, clotrimazole, miconazole, cysteine, glycine, threonine, lidocaine, trypsin, streptokinase, plasmin, streptodornase, deoxyribonuclease, epinephrine, serotonin, amphotericin B, clotrimazole, miconazole, and chlorohexidine digluconate.

In certain embodiments, the present invention relates to the any of the aforementioned materials, wherein the water-soluble particles containing the active agent form at least 10% of the material by weight. In certain embodiments, the present invention relates to the any of the aforementioned materials, wherein the water-soluble particles containing the active agent form at least 20% of the material by weight. In certain embodiments, the present invention relates to the any of the aforementioned materials, wherein the water-soluble particles containing the active agent form at least 30% of the material by weight. In certain embodiments, the present invention relates to the any of the aforementioned materials, wherein the water-soluble particles containing the active agent form at least 40% of the material by weight. In certain embodiments, the present invention relates to the any of the aforementioned materials, wherein the water-soluble particles containing the active agent form at least 50% of the material by weight.

Another aspect of the invention relates to a method for preparing a water-soluble polymer particle impregnated material comprising the steps of: coating a substrate with a plurality of water-soluble polymer particles; stirring a mixture comprising water, surfactant, and a prepolymer mixture; pouring the mixture on the water-soluble polymer particle coated substrate, thereby permeating the substrate, and allowing the mixture to cure into a foam, thereby forming a water-soluble polymer particle impregnated material.

Another aspect of the invention relates to a method for preparing a water-soluble polymer particle impregnated material comprising the steps of: stirring a first mixture comprising water, surfactant, and a prepolymer mixture; pouring the first mixture onto a surface; placing a substrate on top of the first mixture and allowing the first mixture to cure into a first foam layer, thereby binding the substrate and the first foam layer; coating the side of the substrate which is not bound to the first foam layer with a plurality of water-soluble polymer particles; stirring a second mixture comprising water, surfactant, and a prepolymer mixture; pouring the second mixture onto a surface containing the water-soluble polymer particles and allowing the second mixture to cure, thereby trapping the plurality of water-soluble polymer particles within the material and forming a water-soluble polymer particle impregnated material.

In certain embodiments, the present invention relates to the any of the aforementioned methods, wherein the substrate is a non-woven material. In certain embodiments, the present invention relates to the any of the aforementioned methods, wherein the substrate is an aperture non-woven material. In certain embodiments, the present invention relates to the any of the aforementioned methods, wherein the substrate is a non-woven material comprising a mesh surface. In certain embodiments, the present invention relates to the any of the aforementioned methods, wherein the substrate is a non-woven fabric or a non-woven cloth.

In certain embodiments, the present invention relates to the any of the aforementioned methods, wherein the foam is a polyurethane foam prepared from water, a surfactant, and a prepolymer mixture.

In certain embodiments, the present invention relates to the any of the aforementioned methods, wherein the surfactant is selected from the group consisting silcone-based surfactants, polysiloxane-polyoxyalkylene block copolymers, cyanoalkylpolysiloxanes, alkylpolysiloxanes, polydimethylsiloxane, polyoxyalkylene-modified dimethylpolysiloxanes, salts of fatty acids, salts of sulfuric acid esters, salts of phosphoric acid esters and sulfonates, TRITON™ (e.g., octylphenol ethoxylate) materials, TERGITOL™ (e.g., nonylphenol ethoxylate) materials, EMEREST® (glycerol esters with stearic, oleic, and isostearic fatty acids) materials, EMULGADE® (cetearyl alcohol and/or stearate-containing emulsifier) materials, Cocamide monoethanolamine (MEA), PLURONIC® (polyoxyethylene-polyoxypropylene-polyoxyethylene polymer) materials, BRIJ® 72 (polyoxyethylene (2) stearyl ether) and sodium alpha olefin sulfonate. In certain embodiments, the present invention relates to the any of the aforementioned methods, wherein the surfactant is polyoxyalkylene-modified dimethylpolysiloxanes.

In certain embodiments, the present invention relates to the any of the aforementioned methods, wherein the prepolymer mixture selected from the group consisting of branched alkyl-isocyanate-capped poly(ether), unbranched alkyl-isocyanate-capped poly(ether), branched aromatic-isocyanate-capped poly(ether), unbranched aromatic-isocyanate-capped poly(ether), branched alkyl-isocyanate-capped poly(ether)-poly(ester) copolymer, unbranched alkyl-isocyanate-capped poly(ether)-poly(ester) copolymer, branched aromatic-isocyanate-capped poly(ether)-poly(ester) copolymer, and unbranched aromatic-isocyante-capped poly(ether)-poly(ester) copolymer. In certain embodiments, the present invention relates to the any of the aforementioned methods, wherein the prepolymer mixture is toluene diisocyanate terminated or capped polyethylene glycol with less than 6% available unreacted NCO groups and with an isocyanate functionality less than 2.

In certain embodiments, the present invention relates to the any of the aforementioned methods, wherein the water-soluble polymer particles are prepared from one or more monomers selected from the group consisting of styrene, vinyl acetate, ethylene, ethylene oxide, acrylonitrile, acrylic acid, acrylamide, maleic anhydride, monovinyl silicon compounds, ethyl vinyl ether, chlorostyrene vinyl pyridine, vinylidene chloride, butyl vinyl ether, methyl methacrylate and 2-ethylhexyl acrylate In certain embodiments, the present invention relates to the any of the aforementioned methods, wherein the water-soluble polymer particles are polyethylene oxide polymer particles or polyethylene glycol polymer particles.

In certain embodiments, the present invention relates to the any of the aforementioned methods, wherein the active ingredient is selected from the group consisting of silver salts, silver nitrate, silver sulfate, nafcillin, nystatin, undecylenic acid, salicylic acid, salicylsulfonic acid, nicotinic acid, adenosine diphosphate, chlorhexidine, bacitracin, chlortetracycline, gentamycin, kanamycin, neomycin B, polymyxin B, streptomycin, tetracycline, amphotericin B, clotrimazole, miconazole, cysteine, glycine, threonine, lidocaine, trypsin, streptokinase, plasmin, streptodornase, deoxyribonuclease, epinephrine, serotonin, amphotericin B, clotrimazole, miconazole, and chlorohexidine digluconate.

In certain embodiments, the present invention relates to the any of the aforementioned methods, wherein the water-soluble particles containing the active agent form at least 10% of the material by weight. In certain embodiments, the present invention relates to the any of the aforementioned methods, wherein the water-soluble particles containing the active agent form at least 20% of the material by weight. In certain embodiments, the present invention relates to the any of the aforementioned methods, wherein the water-soluble particles containing the active agent form at least 30% of the material by weight. In certain embodiments, the present invention relates to the any of the aforementioned methods, wherein the water-soluble particles containing the active agent form at least 40% of the material by weight In certain embodiments, the present invention relates to the any of the aforementioned methods, wherein the water-soluble particles containing the active agent form at least 50% of the material by weight.

BRIEF DESCRIPTION OF THE FIGURE

FIG. 1 depicts a pictorial representation of a non-woven substrate which has polyethylene oxide particles captured in the "pockets" of the substrate. This material may then be contacted with a foam, thereby forming a material comprising a foam coated substrate, as is described herein.

DETAILED DESCRIPTION

One aspect of the present invention relates to a method for trapping water-soluble polymer particles between a substrate and a hydrophilic or hydrophobic polyurethane foam. In certain embodiments, the water-soluble polymer particles may be spread across a surface of a substrate, including in any apertures, dimples or pockets, and the foam may permeate the substrate and cure, thereby trapping the particles within the material.

However, if a substrate is too thick any foam poured over the top of it would not permeate all the way through the particles and bind them and exposes the risk of any unbound particles falling out of the unfoamed side of said substrate. This is not the case with a substrate with dimples or pockets where the backside of the substrate acts as a barrier to contain any unbound particles. One way of overcoming the thickness problem is to cast a bottom layer of foam, lay down an apertured nonwoven on top of it before it is fully cured so adhesion is achieved, fill the apertures with particles, and again foam on top of the composite. The end result is two foam layers both bonded to an internal layer of nonwoven with its apertures filled with particles. The thickness of the whole is not dependent upon the foam permeating the particles and is now only limited by the thickness of available nonwovens. Therefore, another aspect of the invention relates to such a process (and the materials made thereby): trapping water-soluble polymer particles within a substrate by first coating one side of the substrate with a hydrophilic or hydrophobic polyurethane foam, then placing water-soluble polymer particles on the uncoated side of the substrate, and finally sealing the particles within the material by another layer of foam.

Importantly, when the impregnated foams of the invention are contacted with a liquid, such as water, the water-soluble polymer particles dissolve and release the active ingredients contained therein. In addition, by altering the molecular weight or chemical composition of the water-soluble polymer particles and/or the characteristics of the foam (such as composition and thickness), one skilled in the art to will be able to tune the physical properties of the product to better meet the needs of a specific application (i.e. be able to alter the rate at which the water-soluble polymer particles dissolves and thus releases the active agent contained therein).

Foams

The term "foam" as used herein refers to any lightweight, cellular plastic material containing gas-filled voids. In certain embodiments, the foam material of the invention has a matrix of substantially open cells (pores) formed therein. The foam can have, for example, 20 to 150 pores per inch. In certain embodiments, the foam may have from 50 to 80 pores per inch. In certain embodiments, the impregnated foam can be in the form of a block, strip, sheet or extruded shape.

Typical foams include polyurethanes, polyvinyl chlorides and polyesters. In certain embodiments of the invention, the foam which is impregnated with water-soluble polymer particles is a polyurethane foam.

Hydrophilic and hydrophobic polyurethanes can be made by what is commonly referred to as the "Prepolymer Process." A prepolymer in this context is an isocyanate-capped polyol or polyurethane. In the case of hydrophobic polyurethanes, a hydrophobic polyol is used. In the case of a hydrophilic polyurethane, a hydrophilic polyol, usually a polyethylene glycol, is used. In a typical process, an aqueous phase and the prepolymer are emulsified. A chemical reaction takes place between the water in the aqueous phase and the isocyanates liberating carbon dioxide gas and polymerizing the mass, simultaneously. The quality of the foam is governed in part by the quality of the emulsion that is created. While other factors including temperature and mixing speed also influence the foam structure, it is common to use a surfactant to control foam quality. It is clear that adding another component to the formulation, particularly a surface active ingredient, will affect the foam quality. Once made, however, such hydrophilic and hydrophobic foams are known to be both chemically and physically stable.

A representative sample of suitable hydrophilic prepolymers would include polyether polyols capped with polyfunctional aromatic isocyanates, for example, toluene diisocyanate (TDI) or methylene diphenyl isocyanate (MDI), or with aliphatic isocyanates, for example, isoperone diisocyanate (IPDI) or hydrogenated methylene diphenyl isocyanate (HMDI). The polyether polyols are hydrophilic polyoxyalkylenes with a minimum of about 40 mol % ethylene oxide. Crosslinking sites are developed, when necessary, during the prepolymer formation by the addition of water to the prepolymer polyols to form urea and subsequently biuret linkages in the prepolymer, formation of allophate linkages by prolonged heating at elevated temperatures, branching of prepolymers by the addition of triols or tetrols (for example, trimethylolpropane, glycerol, or pentaerythritol), or formation of branches by the use of selective catalysts.

Hydrophilic prepolymers can be purchased from a number of companies for use in the manufacture of foams. A representative list of prepolymers includes TREPOL® sold by Rynel (discussed below), HYPOL™ sold by Dow, Prepol sold by Lendell Manufacturing, Inc. (St. Charles, Mich.), Hydropol sold by Mace Adhesives & Coatings Co., Inc., AQUAPOL® (isocyanate functional prepolymer of a polyether polyol) sold by Carpenter Co. (Richmond, Va.), and UREPOL® (polyurethane prepolymer) sold by EnviroChem Technologies. These prepolymers are activated by contact with water and it is known that the amount of water can influence the properties of the foam. Typical prepolymer to water ratios range from about 2:1 to about 0.5:1 depending on the desired properties of the resultant polymer.

TREPOL® prepolymer is a polyether urethane prepolymer of toluene diisocyanate terminated or capped polyethylene glycol with less than 6% available unreacted NCO groups and with an isocyanate functionality less than 2. A feature and advantage of the TREPOL® type prepolymer characterized by low density of available NCO reactive sites and isocyanate functionality less than 2 accompanied by only small amounts of monomer or low molecular weight components is that the resulting polymerization with the aqueous phase generates lower exothermic heat permitting limitation of the reaction temperature to the range of for example 120° F. and lower. A further advantage of the TREPOL® prepolymer is that the high water content produces a prepolymer of greater specific heat for more effective dissipation of exothermic heat during reaction. The resulting open foam substrate generated by reaction with the prepolymer with lower density available NCO sites is also characterized by lower toxicity.

A variety of polymeric foams are amenable to the presence invention. Representative examples of polymeric foams are poly(alkyloxy urethane) foams, polycarbonate foams, and poly(oxyether)polyol foams such as polyethylene glycol, polypropylene glycol, or a copolymer of polyethylene glycol and polypropylene glycol.

It is known that hydrophilic polyurethane foams having improved wet strength properties can be prepared from a reaction mixture comprising a select mixture of three polyols. As such, these foams are of particular utility in wet cleaning and scrubbing applications. In preparing these polyurethane foams, the so-called "one-shot method" or the "prepolymer technique" may be used. These foams are prepared from a reaction mixture comprised of an organic polyisocyanate, a foaming agent, a reaction catalyst, and, as the polyol reactant, a select mixture or combination of three polyether polyols. Any organic polyisocyanate which is useful in the preparation of polyurethane foams can be employed in practicing the process. This includes, for example, toluene diisocyanate, such as the 80:20 mixture or the 65:35 mixture of the 2,4- and 2,6-isomers, ethylene diisocyanate, propylene diisocyanate, methylene-bis-4-phenyl isocyanate, 3,3'-bitoluene-4,4'-diisocyanate, hexamethylene diisocyanate, naphthalene-1,5-diisocyanate, polymethylene polyphenylisocyanate, mixtures thereof and the like. A preferred organic polyisocyanate is an aromatic diisocyanate, such as TDI or MDI. The amount of polyisocyanate employed in a process should be sufficient to provide in the range of about one isocyanate group per hydroxyl group present in the reaction system, which includes all the polyol reactants as well as any additive or foaming agent employed. An excess of isocyanate compound may be conveniently employed; however, this is generally undesirable due to the high cost of the isocyanate compounds. It is preferable, therefore, to employ sufficient isocyanate to provide no greater than about 1.25 isocyanate groups per hydroxyl group, and preferably between about 0.9 and about 1.2 isocyanate groups per hydroxyl group. The ratio of isocyanate to OH group times 100 is referred to as the "index." See the following U.S. patents for additional examples: U.S. Pat. No. 3,194,773, U.S. Pat. No. 3,238,273, No. 3,336,242, U.S. Pat. No. 3,380,967, U.S. Pat. No. 3,461,086, U.S. Pat. No. 3,457,203, U.S. Pat. No. 3,546,145., and U.S. Pat. No. 3,457,203.

Surfactants

A variety of surfactants are known in the art and are amenable to the present invention. One type of surfactant is a silcone-based surfactant. Silicone surfactants known in the art include: "hydrolysable" polysiloxane-polyoxyalkylene block copolymers, "non-hydrolysable" polysiloxane-polyoxyalkylene block copolymers, cyanoalkylpolysiloxanes, alkylpolysiloxanes, polydimethylsiloxane, and polyoxyalkylene-modified dimethylpolysiloxanes. The type of silicone surfactant used and the amount required depends on the type of foam produced as recognized by those skilled in the art. Silicone surfactants can be used as such or dissolved in solvents such as glycols. Other types of surfactants amenable to the present invention relate to anionic surfactants such as salts of fatty acids, salts of sulfuric acid esters, salts of phosphoric acid esters and sulfonates, and the like. Certain preferred surfactants are TRITON™ (e.g., octylphenol ethoxylate) materials marketed by Union Carbide, TERGITOL™ (e.g., nonylphenol ethoxylate) materials marketed by Union Carbide, EMEREST® (glycerol esters with stearic, oleic, and isostearic fatty acids) materials marketed by Henkel Corp., EMULGADE® (cetearyl alcohol and/or stearate-containing emulsifier) materials marketed by Henkel Corp., Cocamide MEA marketed by Chemron, PLURONIC® (polyoxyethylene-polyoxypropylene-polyoxyethylene polymer) materials marketed by BASF, BRIJ® 72 (polyoxyethylene (2) stearyl ether) marketed by ICI, and Sodium alpha olefin sulfonate marketed by Witco.

Water-Soluble Polymer Particles

The term "water-soluble polymer particle" as used herein refers to a polymer particle which degrades overtime when in contact with water or another liquid. The particle sizes may range from powder size, for example in the range of 1 to 5 microns, to granular and bead sizes from 2,000 to 5,000 microns.

In certain embodiments, the water-soluble polymer particles are prepared from one or more monomers selected from the group consisting of styrene, vinyl acetate, ethylene, ethylene oxide, acrylonitrile, acrylic acid, acrylamide, maleic anhydride, monovinyl silicon compounds, ethyl vinyl ether, chlorostyrene vinyl pyridine, vinylidene chloride, butyl vinyl ether, methyl methacrylate and 2-ethylhexyl acrylate. In certain embodiments, the water-soluble polymer particles are selected from the group consisting of starch, modified starch, starch derivatives, modified starch derivatives, polyvinyl alcohol, cellulose derivatives, polysaccharide gums, and maltodextrin. In certain embodiments, the water-soluble polymer particles are selected from the group consisting of polyethylene oxide (PEO) and polyethylene glycol (PEG).

The term "impregnated" as used here in means to be contained within. For example, a polyethylene oxide impregnated polyurethane foam is a polyurethane form with polyethylene oxide particles infused throughout.

Active Ingredients

The invention contemplates application of the composite dispensing material for storing, protecting and selectively releasing and dispensing a variety of active or functional liquids, solids and other components collectively referred to herein as "active ingredients." Water-soluble polymer particles containing active ingredients for use in the impregnated foam materials include physiologically- or biologically-active agents, such as antibacterial agents, antifungal agents, analgesic agents, tissue healant agents, local anesthetic agents, antibleeding agents, enzymes or vasoconstrictors. Active ingredients may also be selected from the group consisting of fragrances and antiperspirants. In certain embodiments, the physiologically- or biologically-active agent is selected from the group consisting of: antibacterials selected from the group consisting of silver nitrate, chlorhexidine, Bacitracin, Chlortetracycline, Gentamycin, Kanamycin, Neomycin B, Polymyxin B, Streptomycin, Tetracycline, fusidic acid, pseudomonic acid, and Ceftriaxone (Rocephin); antifungals selected from the group consisting of Amphotericin B, Clotrimazole, Miconazole, nafcillin, Nystatin, and undecylenic acid; tissue healants selected from the group consisting of cysteine, glycine and threonine; analgesics selected from the group consisting of Lidocaine, salicylic acid, salicylsulfonic acid and nicotinic acid; antibleeding agents selected from the group including adenosine diphosphate (such antibleeding agents being such that they make platelets sticky, an initial step required for the stopping of bleeding); enzymes selected from the group consisting of trypsin, Streptokinase, plasmin (Fibrinolysin) and Streptodornase; deoxyribonuclease; and cationic vasoconstrictors selected from the group consisting of epinephrine and serotonin. Such physiologically- or biologically-active agents may be used in the form of their salts.

Substrates

As mentioned above, another embodiment the inventive materials incorporates a substrate (e.g. a nonwoven material) which can be impregnated with particles and interpenetrating (and permeated) by foam. In certain embodiments, the substrate is a nonwoven material which may be of desired contour. When the foam is polymerized in the presence of the substrate, the foam bonds to fibers and fills the interstices of the substrate while the active ingredient water-soluble polymer particles are trapped between the surfaces of the substrate and the foam.

In general, substrate may be any of a multitude of materials including plastic, metal fiber, wood fiber, glass, fiberglass, and textiles. Representative examples include: cotton, wool, silk, jute, linen, rayon, acetate, polyesters, polyethyleneterephthalate, polyamides, nylon, acrylics, olefins, aramids, azlons, glasses, fiberglass, modacrylics, novoloids, nytrils, rayons, sarans, spandex, vinal, vinyon, foams, films, foamed sheets, natural leathers, split hides, synthetic leathers, vinyl, urethane, polyurethane, polyurethane films, polyethylene, polymeric silicon layers, filtration membranes, polysulfones, polyimides, nitrocellulose, cellulose acetate, cellulose, and regenerated cellulose, alginates, hydrocolloids, metalized films, foils, silicones, latex, polycarbonates, and combinations thereof.

Preferred substrates have surfaces which contain apertures or pockets which can be filled with particles, or a structured so that particles can be dispersed within the substrate. Examples of such preferred substrates are aperture nonwoven materials such as Ahlstrom Grade A0568 or 192B (Ahlstrom Head Office—P.O. Box 329, FIN-00101 Helsinki, Salmisaarenaukio 1, FIN-00180 Helsinki, Finland).

Methods of Impregnating a Foam with a Water-Soluble Polymer Particle

One aspect of the invention relates to a method of producing water-soluble polymer particle impregnated materials wherein the particles are trapped by a foam within substrate. In certain embodiments, the water-soluble polymer particles comprise an active ingredient.

For producing such three-component materials the invention provides the method of mixing the aqueous phase and prepolymer phase and dispensing the flowable mixture on a substrate which has been coated with water-soluble polymer particles. Upon foam polymerization the substrate binds to the open foam substrate and interpenetrates and permeates the open foam substrate. In certain embodiments, the foam substrate fills the interstices of the fabric skeleton or matrix with defined density, bonding to the nonwoven fibers and trapping the particles. Such a skeleton or matrix gives added strength to the material and allows for a greater amount of particles to be present than if the particles were simply distributed in the foam.

In certain embodiments, the aqueous phase and prepolymer phase are mixed together in ratio by weight of aqueous phase to prepolymer phase in the range of at least approximately 0.02/1 or greater but preferably in the range of 1/1 to 12/1 and within that range the preferred range of 1/1 to 3/1.

In certain embodiments, the foam may be cured by supporting the substrate on rigid glass or synthetic plastic plates while resting on spaced-apart shelves, or in a pile one atop another, in an oven with air circulation. Importantly, the above curing methods are provided only as examples; other methods of curing foams are well known to those skilled in the art and are contemplated for use herein.

Method of Associating an Active Ingredient with a Water-Soluble Polymer Particle One approach to getting an active ingredient (such as a drug) into the water-soluble polymer particles (such as polyethylene oxide) would be to dissolve (suspend) it in a liquid (such as polyethylene glycol) and then coat it onto the particles. Another approach would be to add the active ingredient directly to a melted water-soluble polymer and then spray-cool the resulting mixture back to a powder (which may then be incorporated into the foam or foam sheet as described herein). Importantly, the above methods of incorporating active ingredients into water-soluble polymer particles are provided only as examples; other methods for incorporating active agents into polymer particles are well known to those skilled in the art and are contemplated for use herein.

EXEMPLIFICATION

The invention now being generally described, it will be more readily understood by reference to the following examples, which are included merely for purposes of illustration of certain aspects and embodiments of the present invention, and are not intended to limit the invention.

Example 1

Polyethylene Oxide Impregnated Polyurethane Foams

Two polyethylene oxide (PEO) impregnated hydrophobic foams (A and B) were made from the components listed in Table 1.

TABLE 1

Polyethylene Oxide Impregnated Hydrophobic Foams Components

| A | B | Component |
| --- | --- | --- |
| 16.3 g | 16.3 g | Bayer Polyether Polyol BAYFIT ® 568B |
| 6.0 g | 9.0 g | Polyethylene Oxide (powder) |
| 0.1 g | 0.1 g | NIAX ™ L-5309 (Union Carbide Silicone Surfactant L5309, a commercially available poly(oxyalkylene)(dimethyl-siloxane) copolymer) |
| 3.0 g | 3.0 g | Bayer Diphenyl Methane Diisocyanate 566A |

The NIAX L-5309 was first mixed with the Bayer Polyether Polyol BAYFIT® 568. Then the polyethylene oxide was added to the mixture. To that mixture was added Bayer diphenylmethane diisocyanate 566A and the resulting four component mixture was stirred with a conventional stirrer. After stirring, the pre-foam mixture was cast between release papers. The dimension between the release papers was 0.032 inches. The foam was initially cast at the 0.032 inches dimension and then rolled with a lab roller to the desired dimension prior to the final cure. This process yielded a product composed of polyurethane foam (A) with 23.6% w/w polyethylene oxide particles dispersed throughout; or (B) with 31.8% w/w polyethylene particles dispersed throughout. While it is believed that one could go as high as about 33% w/w polyethylene particles with the conventional stirrer approach, foams with greater than this amount of particles are not accessible with this methodology.

Interestingly, the fact that the product felt slippery when wet indicated that some of the polyethylene particles were exposed at the surface. It is also safe to assume that some of the particles were in contact with each other within the foam matrix and that since this was an open cell foam that most particles were exposed to the open cells as well. This would mean that if water or liquid was introduced to the foam that most particles would be wetted.

Example 2

Polyethylene Oxide Impregnated Polyurethane Foam Sheets

One approach to addressing the limitation on the amount of particles which can be incorporated into a material buy the method provided in Example 1 is provided below.

In this example, a substrate of nonwoven material was first coated with PEO powder. The coating was accomplished by immersing the substrate in a container of PEO and shaking The result was that the substrate was coated on both sides and PEO particles were captured in the "pockets" of the nonwoven substrate. See FIG. 1.

The substrate was then placed on a sheet of release paper. A mixture of polyurethane pre-polymer (e.g. TREPOL®) and water at a ratio of about 1 to about 1.5 was applied on top of the substrate, which was then covered with another sheet of release paper and the resulting "sandwich" was allowed to cure. After curing, the resulting product was removed from the release paper.

Importantly, it was observed that the polymer/water foam inclusions had permeated the substrate such that it was coated on both sides and such that all of the PEO was trapped within the material. Remarkably, when set, the product exhibited "slippery" characteristics indicated that the now captured PEO was accessible by water.

It was also apparent that the characteristics could be easily modified by different means such as using different substrates. These could include thicker or thinner substrates or substrates with more of fewer "pockets". These substrates could be either woven or nonwoven where the "pockets" could be formed or simply be spaces between the fibers. The substrate could be another foam material where PEO particles could be loaded into the open cells on its surface. Another variation would be a substrate with foam and PEO only on one side so that the uncoated side could be used for bonding to another material. The composite could also be made thicker or thinner, which would change the water or liquid absorption.

One the main advantages of the compositions is that by coating the substrate with the PEO, the difficulties of loading PEO in the polymer or the aqueous portion are eliminated. The substrate also serves to keep the reluctant composite dispersions stable and also can serve as a bonding surface. Electrostatic deposition of the PEO to the substrate is also a possibility.

Example 3

Incorporation of Active Ingredients into Foams and Foam Sheets

Based on the results presented in Example 2, it is proposed a wound dressing or the like could be made in a similar manner but active ingredients could be incorporated into the polyethylene oxide. In the case of an exuding wound, the exudate would dissolve the polyethylene oxide as it wetted, thereby releasing the active ingredient in the process. It is expected that by varying the molecular weight of the polyethylene oxide would also vary the rate at which the polyethylene oxide dissolved and as such would control the rate at which active ingredients are introduced. In addition, other water soluble polymers might be used as active ingredient carriers as well, such as, for example, polyethylene glycol.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A material comprising a substrate, a foam, and a plurality of water-soluble polymer particles,
   wherein each of the plurality of water-soluble polymer particles comprises an active ingredient, the foam binds to the substrate, and the water-soluble polymer particles are trapped between the substrate and the foam.

2. A material comprising a substrate, two layers of foam, and a plurality of water-soluble polymer particles,
   wherein each of the plurality of water-soluble polymer particles comprises an active ingredient, the substrate is sandwiched between the two layers of foam, and the water-soluble polymer particles are trapped between the substrate and at least one of the two layers of foam, wherein said at least one of the two layers of foam binds to the substrate.

3. The material of claim 1 or 2, wherein the substrate is a non-woven material.

4. The material of claim 1 or 2, wherein the foam is a polyurethane foam prepared from water, a surfactant, and a prepolymer mixture.

5. The material of claim 4, wherein the surfactant is selected from the group consisting of silcone-based surfactants, polysiloxane-polyoxyalkylene block copolymers, cyanoalkylpolysiloxanes, alkylpolysiloxanes, polydimethylsiloxane, polyoxyalkylene-modified dimethylpolysiloxanes, salts of fatty acids, salts of sulfuric acid esters, salts of phosphoric acid esters and sulfonates, octylphenol ethoxylate materials, nonylphenol ethoxylate materials, Cocamide monoethanolamine (MEA), polyoxyethylene-polyoxypropylene-polyoxyethylene polymer materials, polyoxyethylene (2) stearyl ether, and sodium alpha olefin sulfonate.

6. The material of claim 4, wherein the prepolymer mixture is selected from the group consisting of branched alkyl-isocyanate-capped poly(ether), unbranched alkyl-isocyanate-capped poly(ether), branched aromatic-isocyanate-capped poly(ether), unbranched aromatic-isocyanate-capped poly(ether), branched alkyl-isocyanate-capped poly(ether)-poly(ester) copolymer, unbranched alkyl-isocyanate-capped poly(ether)-poly(ester) copolymer, branched aromatic-isocyanate-capped poly(ether)-poly(ester) copolymer, and unbranched aromatic-isocyanate-capped poly(ether)-poly(ester) copolymer.

7. The material of claim 4, wherein the prepolymer mixture is toluene diisocyanate-terminated or -capped polyethylene glycol with less than 6% available unreacted NCO groups and with an isocyanate functionality less than 2.

8. The material of claim 1 or 2, wherein the water-soluble polymer particles are prepared from one or more monomers selected from the group consisting of styrene, vinyl acetate, ethylene, ethylene oxide, acrylonitrile, acrylic acid, acrylamide, maleic anhydride, monovinyl silicon compounds, ethyl vinyl ether, chlorostyrene vinyl pyridine, vinylidene chloride, butyl vinyl ether, methyl methacrylate, and 2-ethylhexyl acrylate.

9. The material of claim 1 or 2, wherein the active ingredient is selected from the group consisting of silver salts, silver nitrate, silver sulfate, nafcillin, nystatin, undecylenic acid, salicylic acid, salicylsulfonic acid, nicotinic acid, adenosine diphosphate, chlorhexidine, bacitracin, chlortetracycline, gentamycin, kanamycin, neomycin B, polymyxin B, streptomycin, tetracycline, amphotericin B, clotrimazole, miconazole, cysteine, glycine, threonine, lidocaine, trypsin, streptokinase, plasmin, streptodornase, deoxyribonuclease, epinephrine, serotonin, and chlorohexidine digluconate.

10. The material of claim 1 or 2, wherein the water-soluble particles comprising the active agent represent at least 10% of the material by weight.

11. A method for preparing a water-soluble polymer particle-impregnated material, comprising the steps of:
    coating a substrate with a plurality of water-soluble polymer particles;
    providing a mixture comprising water, surfactant, and a prepolymer mixture;
    dispensing the mixture onto the water-soluble polymer particle-coated substrate; and
    allowing the mixture to cure into a foam, thereby forming a water-soluble polymer particle-impregnated material wherein the water-soluble polymer particles are trapped between the substrate and the foam.

12. The material of claim 1 or 2, wherein the substrate is a non-woven fabric or a non-woven cloth.

13. The material of claim 1, wherein the substrate is an aperture non-woven material and the foam permeates the substrate.

14. A method for preparing a water-soluble polymer particle-impregnated material, comprising the steps of:
    coating a substrate with a plurality of water-soluble polymer particles, wherein the substrate is an aperture non-woven material;
    providing a mixture comprising water, surfactant, and a prepolymer mixture;
    dispensing the mixture onto the water-soluble polymer particle-coated substrate, thereby permeating the substrate; and
    allowing the mixture to cure into a foam, thereby forming a water-soluble polymer particle-impregnated material.

* * * * *